United States Patent [19]

Funatsu

[11] Patent Number: 5,269,790
[45] Date of Patent: Dec. 14, 1993

[54] CLIP FORCEPS

[76] Inventor: Noboru Funatsu, 1008, Act-III, 15-4, Doyama-cho, Kita-ku, Osaka, Japan

[21] Appl. No.: 32,396

[22] Filed: Mar. 15, 1993

Related U.S. Application Data

[63] Continuation of Ser. No. 750,487, Aug. 27, 1991, abandoned.

[30] Foreign Application Priority Data

Oct. 16, 1990 [JP] Japan .................................. 2-109295

[51] Int. Cl.$^5$ ............................................... A61B 17/28
[52] U.S. Cl. .................... 606/142; 606/205; 81/427.5
[58] Field of Search .............. 606/142, 148, 174, 205, 606/206, 210, 51, 52; 433/159; 81/427.5, 415

[56] References Cited

U.S. PATENT DOCUMENTS

| | | | |
|---|---|---|---|
| 385,076 | 6/1888 | Stohlmann | 606/210 |
| 715,612 | 12/1902 | Van Scott | 606/142 |
| 1,741,457 | 12/1929 | Glass | 606/210 |
| 5,022,554 | 3/1991 | Korber | 606/207 X |

OTHER PUBLICATIONS

Mueller "The Surgical Armamentarium" p. 494 (1980).

Primary Examiner—Michael H. Thaler
Attorney, Agent, or Firm—Wenderoth, Lind & Ponack

[57] ABSTRACT

Clip forceps have a pair of clamp members each having a clamp portion and a handle portion extending from the clamp portion. The pair of clamp members cross each other so as to have an X-shaped configuration and are pivotally coupled together at their point of intersection. Grip portions extend from the respective handle portions so that the clamp portions can be moved toward and away from each other by moving the grip portions. Each of the grip portions is curved inwardly, has a semi-oval cross section and has a plurality of projections which provide the outer surface thereof.

2 Claims, 2 Drawing Sheets

CLIP FORCEPS

This application is a continuation of parent application Ser. No. 07/750,487 filed Aug. 27, 1991 and now abandoned.

BACKGROUND OF THE INVENTION

This invention relates to forceps for clamping clips used in surgical operations.

The clips for clipping aneurysms and forceps for clamping such clips are selected by their shape depending on the position of the aneurysm, the visual field of the surgeon and the way in which the operation is performed. But the forceps disclosed in Examined Japanese Patent Publication 61-2705 eliminated the need for stocking clips and forceps of various shapes because with these forceps, clips can be clamped at any desired angle.

To clamp clips at different angles, the forceps have to be held by the hand at different angles. But since most of the conventional forceps have flat grips, it is difficult to turn such forceps. When turning them, they may slip out of the hand of the surgeon, thus exposing the patient to great danger.

SUMMARY OF THE INVENTION

An object of this invention is to provide clip forceps which can be gripped stably without slipping out of one's hand.

In accordance with the present invention, there is provided clip forceps for clamping clips, comprising a pair of clamp members each having a clamp portion, a handle portion extending from the clamp portion, and a grip portion extending from the handle portion, the clamp members crossing each other so as to have an X-shaped configuration and being pivotally coupled together at their point of intersection, the clamp portions being movable toward and away from each other by moving the grip portions toward and away from each other, the grip portions constituting curved portions of the clamp members having concave outer surfaces that extend inwardly, and each of the grip portions having a semi-oval cross-sectional configuration and a plurality of projections defining the outer surfaces thereof.

Since the grip portions are curved inwardly longitudinally they define recesses at the central portions thereof so that they fit any fingers perfectly and are less likely to slip. Further, since each grip has a semi-oval cross-sectional configuration and is formed on the sides thereof with projections, they can be twisted easily without the fear of slipping.

Thus, the operator can concentrate on clipping without the fear of the forceps slipping in the fingers of the operator. This allows the operator to delicately manipulate the forceps.

BRIEF DESCRIPTION OF THE DRAWINGS

Other features and objects of the present invention will become apparent from the following description taken with reference to the accompanying drawings, in which.

DETAILED DESCRIPTION OF THE PREFERRED EMBODIMENT

Figure 1:
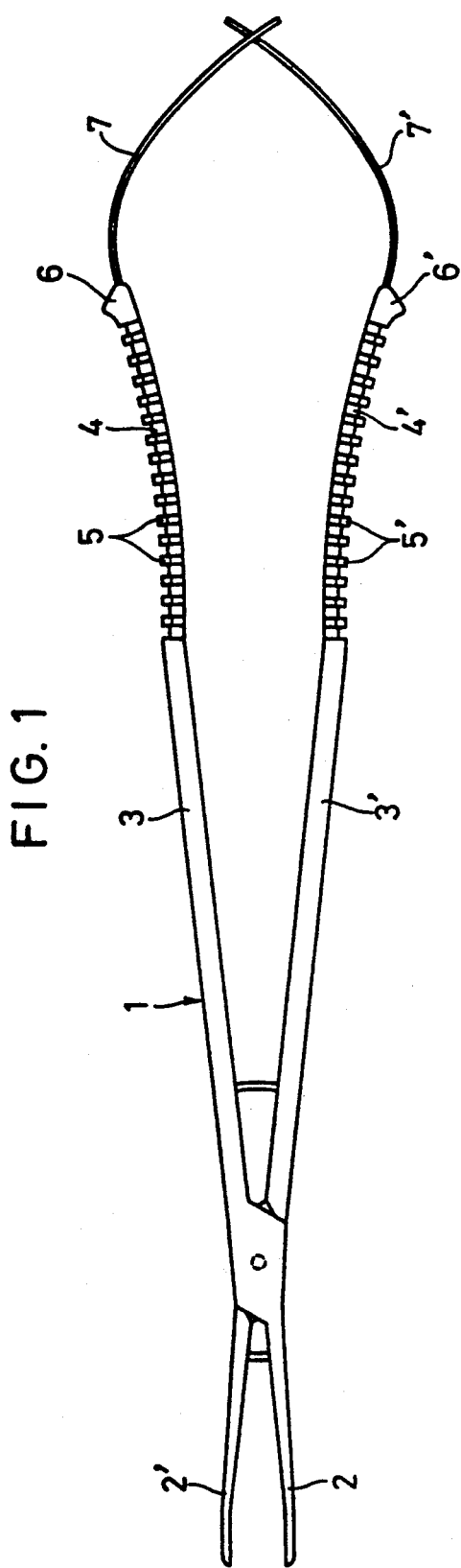
FIG. 1 is a plan view of an embodiment of clip forceps according to this invention.
Figure 2:
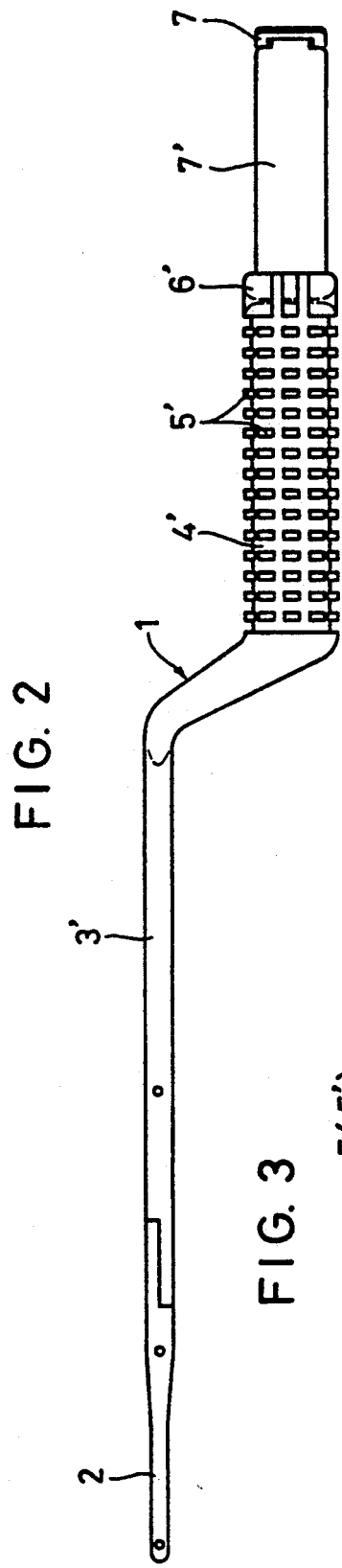
FIG. 2 is a side view of the same.

As shown in FIGS. 1 and 2, the clip forceps 1 comprises a pair of clamp portions 2 and 2' and handles 3 and 3' integral with the clamp portions 2 and 2', respectively. The two members cross each other so as to assume the shape of an X and are pivotally coupled together a their point of intersection.

Figure 3:
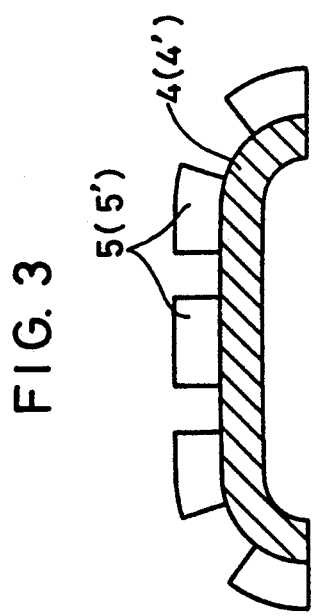
FIG. 3 is an enlarged cross-sectional view of the grips of the same.

Grips 4 and 4' extend from the handles 3 and 3', curving inwardly in a moderate arc in the longitudinal direction. Each grip has substantially a semi-oval cross section as shown in FIG. 3 and is formed on the outer surface with a plurality of relatively large projections 5 or 5'. Further, the grips 4 and 4' are provided at their rear ends with stoppers 6 and 6' from which leaf springs 7 and 7' extend. The ends of the leaf springs 7 and 7' are connected together.

Figure 4:
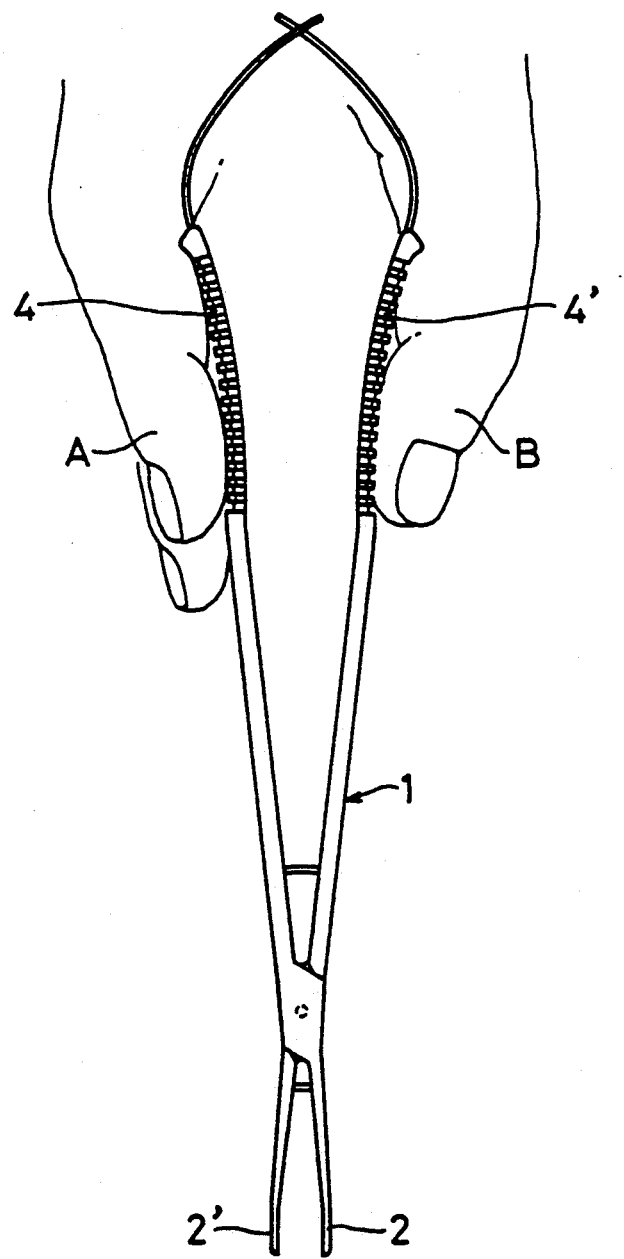
FIG. 4 is a front view showing the same in use.

To use the above-described forceps, as shown in FIG. 4, grips 4 and 4' are gripped by one's fingers A and B. Since the grips 4 and 4' are curved inwardly, they fit onto the fingers A and B like wedges due to the weight of the forceps 1. Thus, the pressing force between the grips and the fingers increases spontaneously. Also, because a plurality of relatively large projections 5 and 5' are provided, the frictional force will increase, too. This prevents the forceps from slipping. The necessary gripping force to be applied to the grips can be minimized. The stoppers 6 and 6' serve to prevent the forceps 1 from slipping off the fingers.

By gripping and pressing the grips 4 and 4' with the fingers A and B, the grips 4 and 4' will move toward each other. The clamp portions 2 and 2' will move toward each other, too. When the pressing force is released, the grips 4 and 4' will move away from each other by the biasing force of the leaf springs 7 and 7' to return to the state shown in FIG. 1.

The clamping portions 2 and 2' and handles 3 and 3' may have shapes other than those shown in the drawings. The leaf springs 7 and 7' may be mounted in various ways.

Any other spring means may be employed in place of the leaf springs 7 and 7'.

What is claimed is:

1. Clip forceps for clamping clips, comprising: a pair of clamp members each having a clamp portion, a handle portion extending from said clamp portion, and a grip portion extending from said handle portion, said clamp members crossing each other at a point of intersection so that the forceps has an X-shaped configuration, and said clamp members being pivotally coupled together at said point of intersection, the clamp portions and the grip portions being located on opposite sides of said point of intersection such that said clamp portions are movable toward and away from each other by moving said grip portions toward and away from each other, said grip portions constituting curved portions of said clamp members, respectively, that have outer surfaces that extend concavely inwardly toward one another as taken in the direction along the lengths of the grip portions, and convex inner surfaces that extend inwardly toward one another as taken in the direction along the lengths of the grip portions, each of said grip portions having a semi-oval cross-sectional configuration as viewed in a plane perpendicular to the length thereof, and each of said grip portions having a main body, a plurality of projections extending from said main body and which constitute the inwardly concave outer surfaces of the grip portions, and a stopper located at an end of the grip portion remote from the handle portion from which the grip portion extends, said stopper projecting outwardly of the outer surface constituted by the projections of the grip portion so as to prevent the forceps from slipping off one's fingers when one's fingers grip the forceps at said outer surfaces.

2. Clip forceps as claimed in claim 1, wherein said projections are dispersed over the entirety of the semi-oval cross-sectional configuration of the grip portions so as to prevent the forceps from slipping relative to one's fingers as the grip portions are held in one's fingers and the forceps is being turned with a twisting motion.

* * * * *